(12) United States Patent
Kim et al.

(10) Patent No.: US 9,588,119 B2
(45) Date of Patent: Mar. 7, 2017

(54) IN VITRO METHOD OF INHIBITING THE GROWTH OF RADIORESISTANT LARYNGEAL CANCER CELLS

(71) Applicant: KOREA INSTITUTE OF RADIOLOGICAL & MEDICAL SCIENCES, Seoul (KR)

(72) Inventors: Jae-Sung Kim, Gyeonggi-do (KR); Sang-Gu Hwang, Seoul (KR); Young-Hoon Han, Seoul (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 0 days.

(21) Appl. No.: 14/746,859

(22) Filed: Jun. 23, 2015

(65) Prior Publication Data

US 2016/0116473 A1    Apr. 28, 2016

(30) Foreign Application Priority Data

Oct. 24, 2014    (KR) .......................... 10-2014-0145085

(51) Int. Cl.
*G01N 33/574*    (2006.01)
*C12N 15/113*    (2010.01)

(52) U.S. Cl.
CPC ... *G01N 33/57407* (2013.01); *C12N 15/1137* (2013.01); *C12Y 503/04001* (2013.01); *C12N 15/113* (2013.01); *C12N 2310/14* (2013.01); *G01N 2333/99* (2013.01)

(58) Field of Classification Search
None
See application file for complete search history.

(56) References Cited

U.S. PATENT DOCUMENTS 7,691,997 B2 *    4/2010    Khvorova ............ A61K 31/713
536/24.5

OTHER PUBLICATIONS

Choe et al., ERp57 modulates STAT3 activity in radioresistant laryngeal cancer cells and serves as a prognostic marker for laryngeal cancer. Oncotarget, 6, 2654-2666, 2015—ePub Jan. 8, 2015).*
Gao et al., Inhibition of STAT3 expression by siRNA suppresses growth and induces apoptosis in laryngeal cancer cells. Acta Pharm. Sinica, 26, 377-383, 2005.*
Aigner et al., Nanoparticle-mediated delivery of small RNA molecules in tumor therapy. Pharmazie, 71, 27-34, 2016.*

* cited by examiner

*Primary Examiner* — Elly-Gerald Stoica
(74) *Attorney, Agent, or Firm* — Revolution IP, PLLC

(57) ABSTRACT

Disclosed are increased expression of ERp57, ERp57-STAT3 complex, and ERp57-STAT3-Mcl-1 in laryngeal cancer, especially in radioresistant laryngeal cancer and their regulations on radioresistance of laryngeal cancer. As such, the efficacy of radiotherapy can be enhanced by diagnosing prognosis in laryngeal cancer and radioresistance of laryngeal cancer. Furthermore, provided are a method of screening a therapeutic agent for laryngeal cancer including selecting a candidate drug that inhibits the expression of ERp57 or inactivates ERp57, and a therapeutic method for inhibiting or treating laryngeal cancer or radioresistant laryngeal cancer, thereby being useful in the treatment of laryngeal cancer.

6 Claims, 4 Drawing Sheets

IN VITRO METHOD OF INHIBITING THE GROWTH OF RADIORESISTANT LARYNGEAL CANCER CELLS

CROSS-REFERENCE TO RELATED PATENT APPLICATION

This application claims the benefit of Korean Patent Application No. 10-2014-0145085 filed on Oct. 24, 2014, in the Korean Intellectual Property Office, the disclosure of which is incorporated herein in its entirety by reference.

BACKGROUND OF THE INVENTION

1. Field of the Invention

The present relates to methods of diagnosing laryngeal cancer or diagnosing prognosis in radioresistance of laryngeal cancer.

2. Description of the Related Art

Radiotherapy is the standard treatment for laryngeal cancer which is the most common cancer occurring on a head and a neck. However, a large number of patients with laryngeal cancer still suffer from local recurrences after radiotherapy, due to the survival of a small fraction of radioresistant tumor cells during the course of radiation therapy.

Thus, to improve the efficacy of radiotherapy, studies have done on drugs that inhibit molecular targets contributing to the radioresistance of tumor cells. Accordingly, it is confirmed that several molecular targets modulate tumor survival and microenvironment have been shown to influence the outcome of radiotherapy. However, relevant targets and signaling pathways are clinically still unclear.

Signal transducer and activator of transcription 3 (STAT3) is a cytoplasmic transcription factor that transmits oncogenic signals from cytokines and growth-factor receptors to the nucleus.

Overexpression of STAT3 in response to the aberrant activation of upstream receptor signals is frequently observed in a variety of cancers including head and neck cancer.

Persistent STAT3 activation promotes the growth and survival of tumor cells through modulation of cell cycle regulators, e.g., cyclin D1, cyclin D2, and c-Myc, upregulation of anti-apoptotic proteins, e.g., myeloid cell leukemia-1 (Mcl-1), B-cell lymphoma 2-like 1 (Bcl-xl), and survivin, downregulation of the tumor suppressor p53, and induction of angiogenesis by vascular endothelial growth factor (VEGF). That is, these mechanisms eventually contribute to resistance to anti-cancer drugs.

In addition, recent reports indicate that Janus Kinase (JAK)/STAT signaling contributes to tumor resistance by modulating not only cell survival but also the tumor microenvironment, including tumor hypoxia and immunity.

Thus, studies on STAT3 activation are essential subjects for overcoming tumor resistance to chemotherapy and radiotherapy.

ERp57, which is also known as protein disulfide isomerase family A member 3 (PDIA3) or glucose-regulated protein 58 (GRP58), belongs to the family of protein disulfide isomerases, and is known as a multifunctional chaperone that regulates proper folding of glycoproteins. In addition, ERp57 also participates in the assembly of major histocompatibility complex class 1 in the endoplasmic reticulum (ER).

In the related art, a gene encoding ERp57 or calreticulin (CRT)/caltexin (CNX) protein, a transformant prepared by transfecting a cell producing a target protein with an expression vector containing the gene that encodes ERp57 or CRT/CNX protein, and a method for mass-production of the target protein by culturing the transformant with different concentrations of tetracycline have been disclosed (refer to Patent document 1).

However, the roles of ERp57 and the correlation between ERp57 and STAT3 in laryngeal cancer, especially radioresistant laryngeal cancer, have not been reported yet.

SUMMARY OF THE INVENTION

Provided is a biomarker composition for diagnosing laryngeal cancer.

Provided is a method of diagnosing prognosis in radioresistance of laryngeal cancer.

Provided is a method of screening a therapeutic agent for radioresistant laryngeal cancer.

Provided is a method of inhibiting or treating radioresistant laryngeal cancer, comprising administering a therapeutically effective amount of an ERp57 inhibitor.

Provided is a method of inhibiting or treating radioresistant laryngeal cancer, comprising administering therapeutically effective amount of an ERp57-STAT3 complex inhibitor.

Additional aspects will be set forth in part in the description which follows and, in part, will be apparent from the description, or may be learned by practice of the presented exemplary embodiments.

According to an aspect of an exemplary embodiment, a method of diagnosing laryngeal cancer cell includes detecting ERp57 or ERp57-signal transducer and activator of transcription 3 (STAT3) complex in a sample.

According to another aspect of an exemplary embodiment, a method of diagnosing prognosis in radioresistance of laryngeal cancer includes detecting ERp57 or ERp57-STAT3 complex in a sample.

According to another aspect of an exemplary embodiment, a method of screening a therapeutic agent for radioresistant laryngeal cancer includes selecting a candidate drug that inhibits expression or activation of ERp57.

According to another aspect of an exemplary embodiment, a method of inhibiting or treating laryngeal cancer includes administering a therapeutically effective amount of an ERp57 inhibitor.

According to another aspect of an exemplary embodiment, a method of inhibiting or treating radioresistant laryngeal cancer including administering a therapeutically effective amount of an ERp57-STAT3 complex inhibitor.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION OF THE INVENTION

Figure 1:
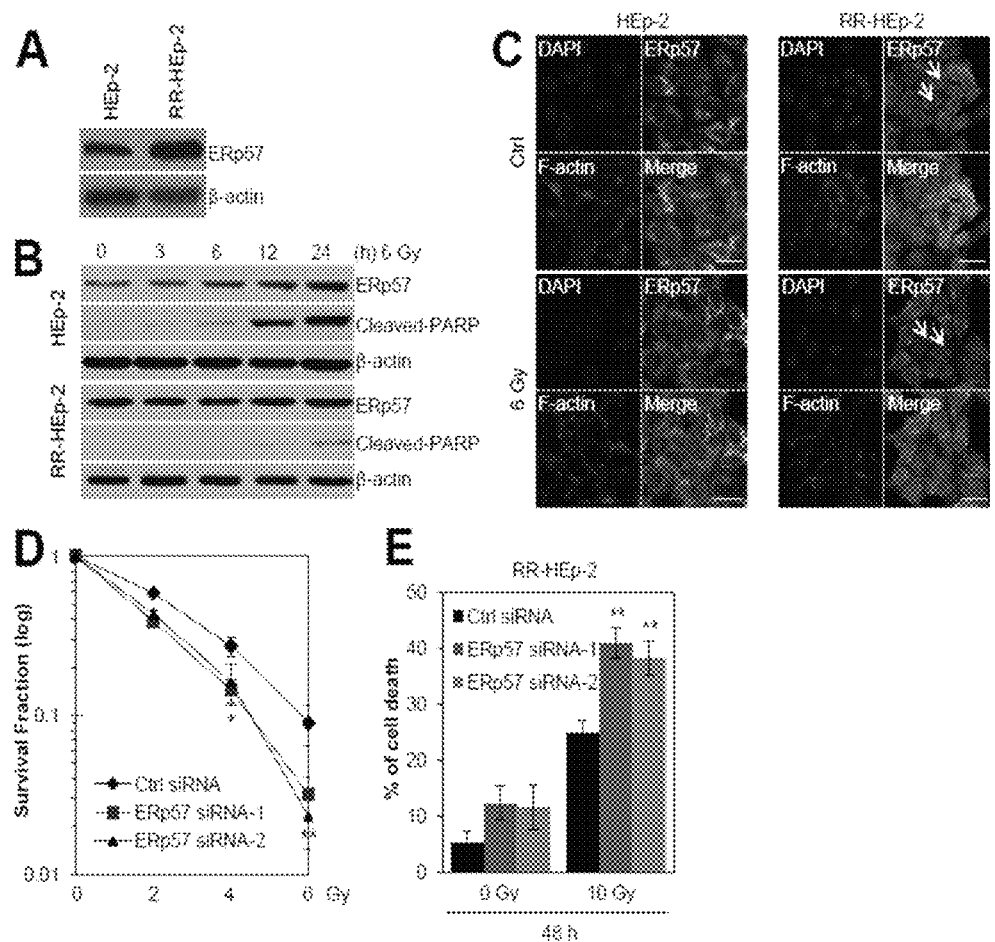
FIG. 1 shows the results of analyzing roles of ERp57 in radioresistance of laryngeal cancer cells. A of FIG. 1 shows the results of immunoblot identifying the expression of ERp57 in laryngeal cancer cells and radioresistant laryngeal cancer cells; B of FIG. 1 shows the results of immunoblot of laryngeal cancer cells and radioresistant laryngeal cancer cells after performing irradiation (6 Gy) for 24 hours; C of FIG. 1 shows the results of staining the laryngeal cancer cells and the radioresistant laryngeal cancer cells of B of FIG. 1, by using anti-ERp57 antibodies (green), Alexa 568 phalloidin (red), and 4', 6'-diamidine-2'-phenylindole dihydrochloride (DAPI, blue); and D and E of FIG. 1 show the results of performing irradiation to ERp57-depleted cells.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. Expressions such as "at least one of," when preceding a list of elements, modify the entire list of elements and do not modify the individual elements of the list.

Hereinafter, the present inventive concept will be described in detail.

When studying roles of ERp57 in radioresistance of laryngeal cancer cells, the inventors of the present inventive concept found that ERp57 regulates activity of signal transducer and activator of transcription 3 (STAT3), and expression of ERp57 and ERp57-STAT3 complex and interaction between ERp57, STAT3, and Mcl-1 are associated with radioresistance of laryngeal cancer, thereby completing the present inventive concept.

The inventors of the present inventive concept also found that ERp57 and ERp57-STAT3 complex are expressed in laryngeal cancer cells, especially in radioresistant laryngeal cancer cells.

Thus, according to an exemplary embodiment of the present inventive concept, provided is a method of diagnosing laryngeal cancer, the method including detecting ERp57 or ERp57-STAT3 complex in a sample.

According to another exemplary embodiment of the present inventive concept, provided is a method of diagnosing prognosis in radioresistance of laryngeal cancer, the method including detecting ERp57 or ERp57-STAT3 complex in a sample.

The expression of ERp57 or ERp57-STAT3 complex in a sample may be detected by antibodies of ERp57 or ERp57-STAT3 complex, but is not limited thereto.

According to another exemplary embodiment of the present inventive concept, provided is a method of providing information for diagnosing prognosis in radioresistance of laryngeal cancer, the method including detecting ERp57 or ERp57-STAT3 complex in a sample by using antibodies of ERp57 or STAT3.

Here, the sample may be tissue lysates, but is not limited thereto.

According to another exemplary embodiment of the present inventive concept, provided is a method of screening a therapeutic agent for radioresistant laryngeal cancer, the method including selecting a candidate drug that inhibits expression of ERp57 or inactivates ERp57.

The method of screening may further include: treating a sample of a suspected patient with radioresistant laryngeal cancer with a candidate drug; and analyzing expression or activity of ERp57 in the candidate drug-treated sample.

According to another exemplary embodiment of the present inventive concept, provided is a method of inhibiting or treating radioresistant laryngeal cancer, the method including administering a therapeutically effective amount of an ERp57 inhibitor.

Here, the ERp57 inhibitor is one selected from siRNA, shRNA, or antisense oligonucleotide, each of which inhibits the expression of ERp57; and an neutralizing antibody which specifically binds to ERp57 and inhibits the ERp57 activity. More preferably, the Erp57 inhibitor may be siRNA that inhibits the expression of Erp57, but is not limited thereto.

The siRNA that inhibits the expression of ERp57 may have a base sequence of SEQ ID NOs: 1 or 2.

According to another exemplary embodiment of the present inventive concept, provided is a method of inhibiting or treating radioresistant laryngeal cancer, the method including administering a therapeutically effective amount the ERp57-STAT3 complex inhibitor.

Here, the ERp57-STAT3 complex inhibitor is one selected from siRNA, shRNA, or antisense oligonucleotide, each of which inhibits the expression of STAT3; and a neutralizing antibody that specifically binds to STAT3 to inhibit the STAT3 activity. More preferably, the ERp57-STAT3 complex inhibitor may be siRNA that inhibits the expression of STAT3, but is not limited thereto.

The siRNA that inhibits the expression of STAT3 may have a base sequence of SEQ ID NO: 3.

Hereinafter, the present inventive concept will be described in further detail with reference to the following examples. These examples are for illustrative purposes only and are not intended to limit the scope of the present inventive concept.

EXAMPLE 1

Cell Preparation and Analysis Method

1. Culture of Laryngeal cancer Cell Line and Radiation Treatment

Human laryngeal squamous cell carcinoma Hep-2 cells were purchased from the American Type Culture Collection (Manassas, Va.). The Hep-2 cells were grown in DMEM supplemented with 10% fetal bovine serum (HyClone, South Logan, Utah) at a temperature of 37° C. in a 5% $CO_2$ incubator. The cultured Hep-2 cells were irradiated using a $^{137}$cesium (Cs) ray source (Atomic energy of Canada Ltd., Mississauga, Canada) at a dose rate of 3.81 Gy/min.

2. Clonogenic Assay

The Hep-2 cells prepared in Example 1-1 were treated with various doses of radiation, and then, the irradiated Hep-2 cells were seeded in triplicate in 60-mm tissue culture dishes at various densities (200 cells for control, 400 cells for 2 Gy, 1500 cells for 4 Gy, and 3000 cells for 6y). After 10 to 14 days, the colonies were fixed with methanol and stained with a Trypan blue solution. Only colonies containing more than 50 cells were counted.

3. RNA Interference

The siRNAs were synthesized at Genolution Pharmaceuticals Inc. (Seoul, Korea). The sequences of siRNAs against human ERp57, STAT3, and Mcl-1 were as follows: ERp57-#1, 5'-GGACAAGACUGUGGCAUAU-3' (SEQ ID NO: 1); ERp57-#2, 5'-GGGCAAGGACUUACUUAUU-3' (SEQ ID NO: 2); STAT3, 5'-CCAACGACCUGCAGCAAUA-3' (SEQ ID NO: 3); and Mcl-1, 5'-CCCGCCGAAUU-CAUUAAUUUA-3' (SEQ ID NO: 4). A non-targeting siRNA (Genolution Pharmaceuticals Inc.) was used as a negative control. Transfection of siRNA was performed using Lipofectamine 2000 (Invitrogen, Carlsbad, Calif.), according to the manufacturer's protocol.

4. Western Blot Analysis

Proteins were separated by sodium dodecyl sulfate (SDS)-polyacrylamide gel electrophoresis (PAGE), transferred to a nitrocellulose membrane, and then, subjected to reactions using rabbit polyclonal anti-phospho-STAT3 (Tyr705), anti-phospho-STAT3 (Ser727), and anti-cleaved-PARP (Asp214) from Cell Signaling Technology (Beverly, Mass.) as well as mouse monoclonal anti-cyclin D1, anti-Mcl-1, anti-ERp57, and anti-STAT3 from Santa Cruz Biotechnology Inc. (Santa Cruz, Calif.) and anti-p53 and anti-β-actin from Sigma. Afterwards, the proteins were subjected to reactions using secondary antibodies (Santa Cruz Biotechnology Inc, CA.) derived from a horseradish peroxidase (HRP)-conjugated mouse or rabbit, and then, blots detecting the proteins were developed using chemiluminescence (ECL) detection system (Amersham Life Science, Piscataway, N.J.).

5. Reverse Transcription Polymerase Chain Reaction (RT-PCR)

Total RNA isolated using STAT-60 (Tel-Test B, Inc., Friendswood, Tex.) was reverse-transcribed with Improm-II™ reverse transcription system (Promega, Madison, Wis.). The PCR primers used herein were as follows: ERp57, sense 5'-CCTGGTGTGGACACTGCAAG-3' (SEQ ID NO: 5) and antisense 5'-CCCTCAAGTTGCTGGCTGCT-3' (SEQ ID NO: 6); IL-6, sense 5'-CCTGAGAAAGGAGACATG-TAACAAGA-3' (SEQ ID NO: 7), and antisense 5'-GGCAAGTCTCCTCATTGAATCC-3' (SEQ ID NO: 8); Mcl-1, sense 5'-ATCTCTCGGTACCTTCGGGAG-3' (SEQ ID NO: 9) and antisense 5'-ACCAGCTCCTACTCCAG-CAAC-3' (SEQ ID NO: 10); VEGF, sense 5'-CGAAGTG-GTGAAGTTCATGGATG-3' (SEQ ID NO: 11) and antisense 5'-TTCTGTATCAGTCTTTCCTGGTGAG-3' (SEQ ID NO: 12); and glyceraldehyde 3-phosphate dehydrogenase (GAPDH), sense 5'-CATCTCTGCCCCCTCT-GCTGA-3' (SEQ ID NO: 13) and antisense 5'-GGATGAC-CTTGCCCACAGCCT-3' (SEQ ID NO: 14).

6. STAT3 Transcriptional Activity Measurement

The cells were co-transfected with 21pSTAT3-TA-Luc and control siRNA or ERp57 siRNA for 48 hours using Lipofectamine 2000 (Invitrogen), and then, untreated or irradiated with 6 Gy. After 24 hours, the cells were harvested using passive lysis buffer, and luciferase activity was evaluated using the Dual Luciferase Reporter Assay Kit (Promega) on a Wallac Victor2 plate reader (Perkin Elmer Corp., Norwalk, Conn.).

7. Cell Death Analysis

The Hep-2 cells prepared in Example 1-1 were harvested using trypsin, washed, and then, incubated with propidium iodide (5 μg/mL) for 10 minutes at room temperature. Afterwards, the cells were analyzed with the FACScan flow cytometer (Becton Dickson, Franklin Lakes, N.J.).

8. Immunohistochemistry

Human tissue microarrays were purchased from SuperBioChips (Cat Number: CH3; Seoul, Korea) and AccuMax (Cat Number: A220; Seoul, Korea).

Immunohistochemical staining was performed with an anti-ERp57 rabbit polyclonal antibody (1:100 dilution; Santa Cruz Biotechnology Inc.), anti-Mcl-1 rabbit polyclonal antibody (1:100 dilution; Santa Cruz Biotechnology Inc.), or anti-phospho-STAT3 (Tyr705) rabbit polyclonal antibody (1:50 dilution; GeneTex, Irvine, Calif.).

Immunostaining was performed with the avidin-biotin-peroxidase method, and staining intensity was scored as follows: 0 (no visible staining), 1+ (faint staining), 2+ (moderate staining), and 3+ (strong staining).

9. Immunoprecipitation

Cells were lysed with nonyl phenoxypolyethoxylethanol-40 (NP-40), and the lysates were then precipitated with a negative control mouse antibody (Santa Cruz Biotechnology Inc.) or a mouse monoclonal antibody against ERp57 (Santa Cruz Biotechnology Inc.). Afterwards, immune complexes were collected using protein G-Sepharose and washed 3 times, and SDS sample buffer was added thereto. The samples were size-fractionated by electrophoresis.

10. Proximity Ligation Assay (PLA)

The paraformaldehyde-fixed cells were permeabilized with 0.2% Triton X-100, washed, and then, blocked with blocking solution (Olink Bioscience, Uppsala, Sweden).

Antigen-retrieved cancer tissues (SuperBioChips) were incubated with 3% hydrogen peroxide, washed, and then, blocked with blocking solution. A mouse monoclonal anti-ERp57 antibody (Santa Cruz Biotechnology Inc.; 1:200 dilution) and a rabbit polyclonal anti-STAT3 antibody (Santa Cruz Biotechnology Inc.; 1:200 dilution) were used for the PLA. The assay was performed using the Duolink Detection Kit with a pair of nucleotide-labeled secondary antibodies (Olink Bioscience). Amplified PLA signals were analyzed using confocal microscopy and quantified using CellProfiler software.

11. Statistical Analysis

The correlation between ERp57 and Mcl-1 immunointensity was analyzed using a Spearman's rank correlation test.

A two-tailed Student's t-test was performed to analyze statistical differences between groups. Here, P<0.05 was considered statistically significant.

EXAMPLE 2

Analysis of Roles of ERp57 in Radioresistance of Laryngeal Cancer Cells

The expression pattern of ERp57 in response to irradiation in laryngeal cancer Hep-2 cells and radioresistant laryngeal cancer Hep-2 (RR-Hep-2) cells was first examined to investigate roles of ERp57 in radioresistance of laryngeal cancer cells. As shown in A of FIG. 1, it was confirmed that ERp57 was upregulated in the RR-Hep-2 cells compared to the Hep-2 cells. As shown in B of FIG. 1, it was also confirmed that ERp57 was gradually upregulated over time in the Hep-2 cells in response to irradiation, whereas its expression was consistently observed in the RR-Hep-2 cells, suggesting that the differential expression pattern of ERp57 was involved in radioresistance of laryngeal cancer cells. In addition, the cellular localization of ERp57 was examined in response to irradiation in the HEp-2 cells and the RR-HEp-2 cells. Because co-localization of ERp57 and calreticulin in the plasma membrane was known to be involved in immunogenic cell death during chemotherapy.

As shown in C of FIG. 1, ERp57 did not translocate to the plasma membrane in response to irradiation, whereas ERp57 was detected in the nuclei of the RR-HEp-2 cells but not in the nuclei of the Hep-2 cells, implying that the nuclear function of ERp57 was associated with the radioresistance.

Next, the survival of the cells in response to irradiation was examined after performing depletion of ERp57 by siRNA. As shown in D of FIG. 1, it was confirmed that depletion of ERp57 reduced the survival of the RR-Hep-2 cells in response to various doses of radiation. As shown in E of FIG. 1, it was also confirmed that radiation-induced cell death was increased.

EXAMPLE 3

Correlation between Radioresistance of Laryngeal Cancer and Interaction between ERp57 and STAT3

The molecular interaction between ERp57 and STAT3 and may be linked with radioresistance of laryngeal cancer as analyzed using immunoprecipitation experiments.

Figure 2:
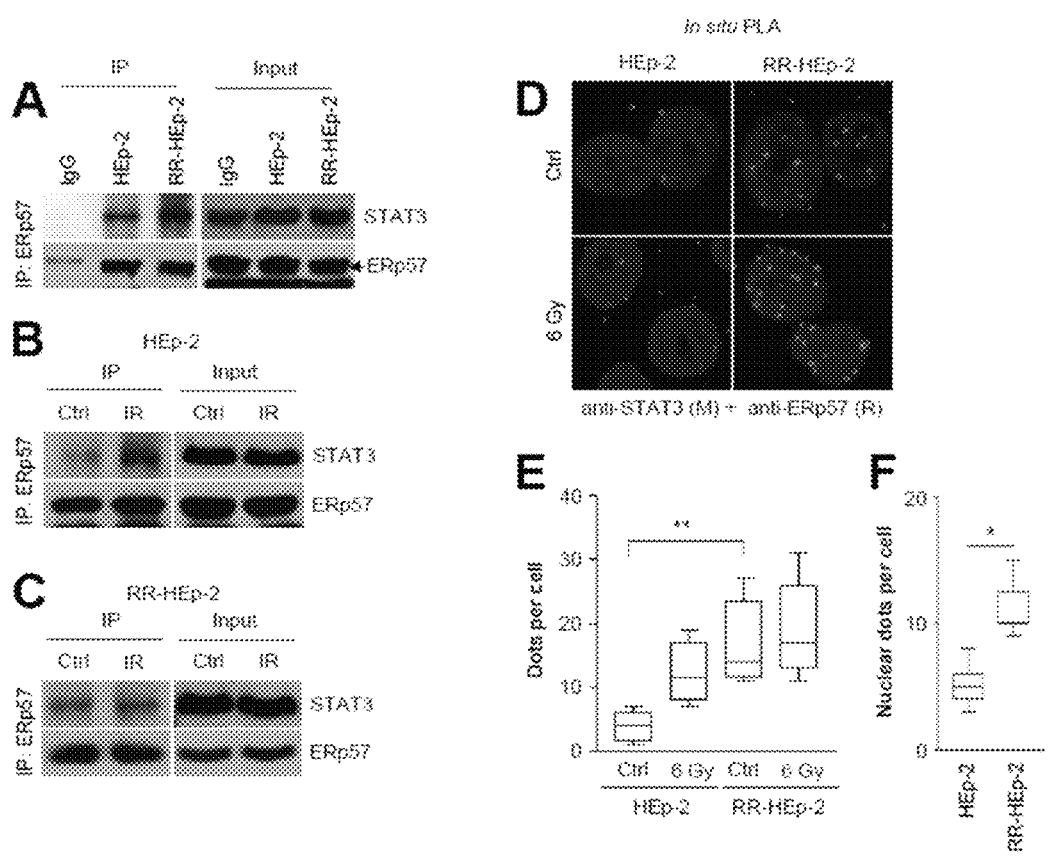
FIG. 2 shows the results regarding interaction between ERp57 and STAT3 and radioresistance of laryngeal cancer cells A to C of FIG. 2 show the results of immunoprecipitation by using anti-STAT3 antibodies or anti-ERp57 antibodies in laryngeal cancer cells and radioresistant laryngeal cancer cells; D of FIG. 2 shows a confocal image obtained by proximity ligation (PLA) analysis using anti-STAT3 antibodies or anti-ERp57 antibodies; and E and F of FIG. 2 show the results of analyzing positive signals of the image of D of FIG. 2 by using Cellprofiler software.

As shown in A of FIG. 2, it was confirmed that the physical interaction between the two proteins was increased in the RR-Hep-2 cells, compared with the Hep-2 cells. In addition, as shown in B and C of FIG. 2, the interaction between the two proteins was differentially modulated in the RR-Hep-2 cells compared to the Hep-2 cells, implying that the differential molecular affinity between the two proteins in response to irradiation may be associated with radioresistance.

Furthermore, the interaction between ERp57 and STAT3 was confirmed by PLA, which visualizes in vivo interactions between the two proteins by using confocal microscopy and quantifies using Cellprofiler software.

Consistent with the results of the co-immunoprecipitation experiment as shown in D and E of FIG. 2, more positive signals indicating interactions between the two proteins were observed in the RR-Hep-2 cells than in the Hep-2 cells. In particular, as shown in F of FIG. 2, the interactions in the irradiated cells were increased in the nucleus of the RR-Hep-2 cells, suggesting that the increased ERp57-STAT3 interaction was associated with the radioresistance of laryngeal cancer cells.

EXAMPLE 4

Analysis of ERp57-Regulated STAT3 Activity in Radioresistant Laryngeal Cancer Cells To analyze the ERp57-regulated STAT3 activity in radioresistant laryngeal cancer cells, the expression levels of phosphorylated STAT3 and its target gene such as Mcl-1, cyclin D1, and p53 in the Hep-2 cells and the RR-Hep-2 cells were examined.

Figure 3:
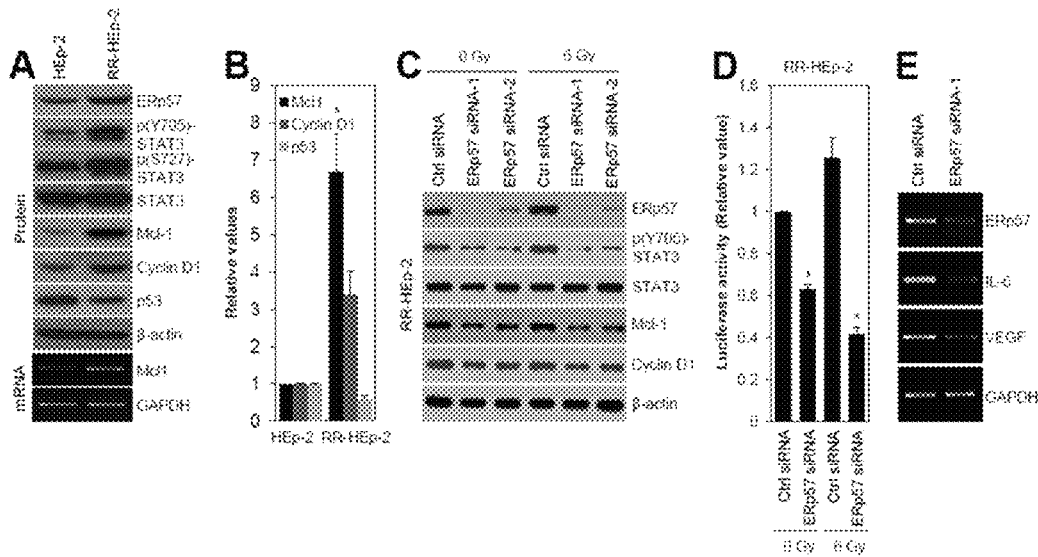
FIG. 3 shows the results regarding ERp57-regulated STAT3 activity in radioresistant laryngeal cancer cells. A of FIG. 3 shows the immunoblot result regarding laryngeal cancer cells and radioresistant laryngeal cancer cells; B of FIG. 3 shows the results of quantifying the extent of expression of Mcl-1, cyclin D1, and p53 by using Image J software; C of FIG. 3 shows the immunoblot result obtained after performing irradiation to ERp57-depleted cells; D of FIG. 3 shows the result of analyzing STAT3 activity in radioresistant laryngeal cancer cells; E of FIG. 3 shows the results obtained by performing reverse transcription polymerase chain reaction (RT-PCR) to identify expression of Interleukin-6 (1L-6), vascular endothelial growth factor (VEGF), and glyceraldehyde-3-phosphate dehydrogenase (GAPDH) in ERp57-depleted cells.

As shown in A of FIG. 3, it was confirmed that the phosphorylated STAT3 and its target genes, e.g., Mcl-1 and cyclin D1, were augmented in the RR-Hep-2 cells compared to the Hep-2 cells, whereas p53 was downregulated by STAT3. Furthermore, as a result of quantifying the expression strength as shown in B of FIG. 3, the expression levels of Mcl-1 and cyclin D1 were increased in the RR-Hep-2 cells, except in the case of p53.

To determine the regulatory effect of ERp57 on STAT3 activity, ERp57 was depleted in the RR-Hep-2 cells with siRNA, followed by being irradiated with 6 Gy. As shown in C of FIG. 3, ERp57 depletion decreased the phosphorylated STAT3 and expression of its target genes such as Mcl-1 and cyclin D1, and as shown in D of FIG. 3, inhibited STAT3 activity, indicating that ERp57 enhanced STAT3 activity in radioresistant laryngeal cancer cells.

Moreover, as shown in E of FIG. 3, ERp57 depletion also decreased the expression of STAT3-regulated cytokines such as interleukin-6 (IL-6) and vascular endothelial growth factor (VEGF).

EXAMPLE 5

Analysis of ERp57-STAT3-Mcl-1 Axis in Radioresistance of Laryngeal Cancer Cells

First, to investigate STAT activity in the RR-Hep-2 cells, the RR-Hep-2 cells were treated with S31-201 which is a direct STAT3 inhibitor, and then, irradiated with 6 Gy and 10 Gy.

Figure 4:
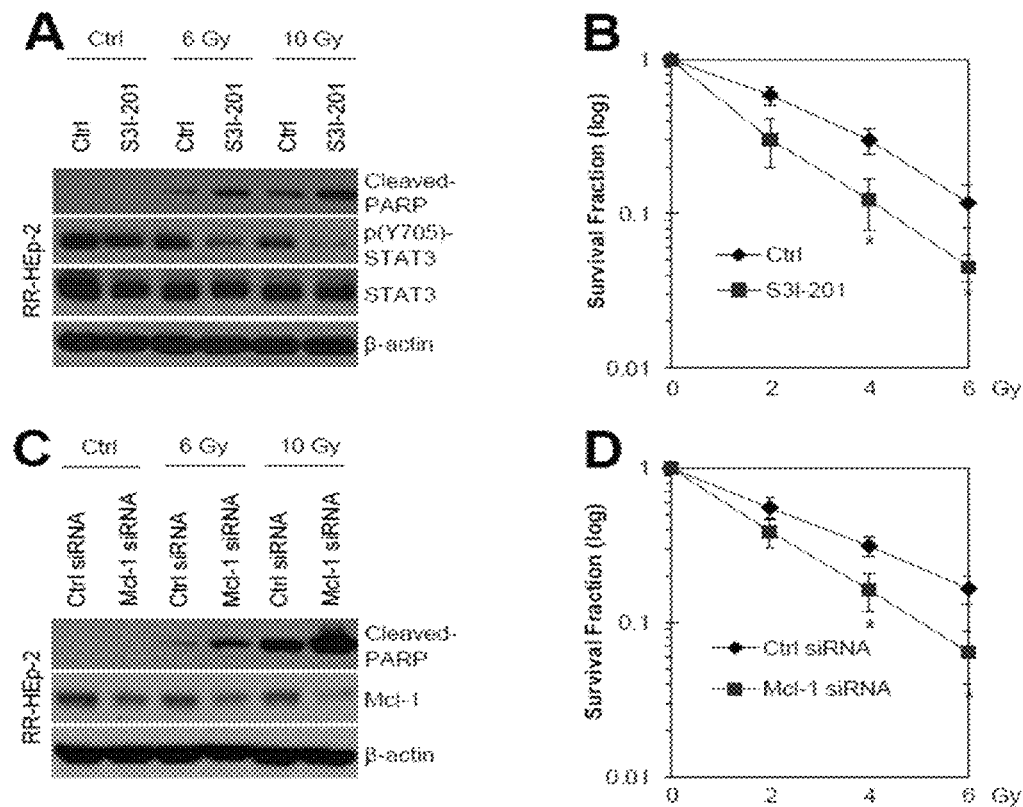
FIG. 4 shows the graphs analyzing inhibition of STAT3 and radioresistance of laryngeal cancer cells. A of FIG. 4 shows the immunoblot result obtained by irradiating STAT3-depleted cells; B of FIG. 4 is a graph showing the survival of the cells obtained by performing irradiation to STAT3-depleted cells; C of FIG. 4 shows the immunoblot result obtained by performing irradiation to Mcl-1-depleted cells; and D of FIG. 4 is a graph showing the survival of the cells obtained by performing irradiation to Mcl-1-depleted cells.

As shown in A of FIG. 4, the phosphorylation of STAT3 was significantly decreased while the radiation-induced cell death of the RR-Hep-2 cells was significantly increased. As shown in B of FIG. 4, the survival of the RR-Hep-2 cells was reduced in response to various doses of radiation, indicating that STAT3 activity was important for the radioresistance of laryngeal cancer cells.

Next, to investigate Mcl-1 activity in the RR-Hep-2 cells, the RR-Hep-2 cells were treated with Mcl-1 siRNA, and then, irradiated with 6 Gy and 10 Gy. Similar to the effect of STAT3 inhibition, as shown in C of FIG. 4, Mcl-1 depletion also increased the radiation-induced cell death of the RR-Hep-2 cells. In addition, as shown in D of FIG. 4, Mcl-1 depletion also reduced the survival of the RR-Hep-2 cells in response to various doses of radiation, suggesting that ERp57-STAT3-Mcl-1 regulation was important for the radioresistance of laryngeal cancer.

EXAMPLE 6

Analysis of Interactions between ERp57, STAT3, and Mcl-1 in Laryngeal Cancer Tissues To investigate the physical relevance of ERp57-STAT3-Mcl-1 regulation in laryngeal cancer tissues, the expression levels of ERp57 and the phosphorylated STAT3 in laryngeal cancer were examined.

Figure 5:
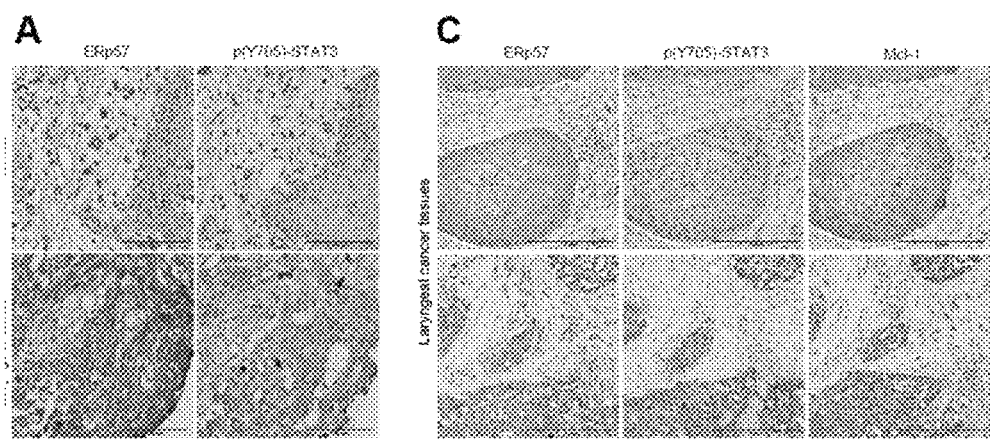
FIG. 5 shows the results of analyzing relevance of interactions between ERp57, STAT3, and mcl-1 in radioresistant laryngeal cancer tissues. A of FIG. 5 shows immunostaining images regarding ERp57 and phosphorylated STAT3 in normal tissues and laryngeal cancer tissues; B of FIG. 5 shows the table classifying the results according to the staining intensity; and C of FIG. 5 shows immunostaining images regarding ERp57, phosphorylated STAT3, and Mcl-1 in laryngeal cancer tissues.

As shown in A of FIG. 5, it was confirmed that the expression levels of ERp57 and the phosphorylated STAT3 were increased in laryngeal cancer cells compared with normal cells.

Furthermore, the expression of ERp57 and Mcl-1 was examined by using tissue microarrays including 59 laryngeal tumor tissues. As shown in B of FIG. 5 based on Spearman's correlation analysis, it was confirmed that the expression of ERp57 strongly correlated with the expression of Mcl-1. In addition, as shown in C of FIG. 5, staining patterns of ERp57 with those of the phosphorylated STAT3 or Mcl-1 were also similar in serial sections of the same tissue.

EXAMPLE 7

Correlation between Poor Prognosis in Laryngeal Cancer and Interactions between ERp57 and STAT3

To investigate the correlation between poor prognosis in laryngeal cancer and interactions between ERp57 and STAT3, in vivo interactions of ERp57 and STAT3 in laryngeal cancer tissues were verified by in situ PLA assay.

Figure 6:
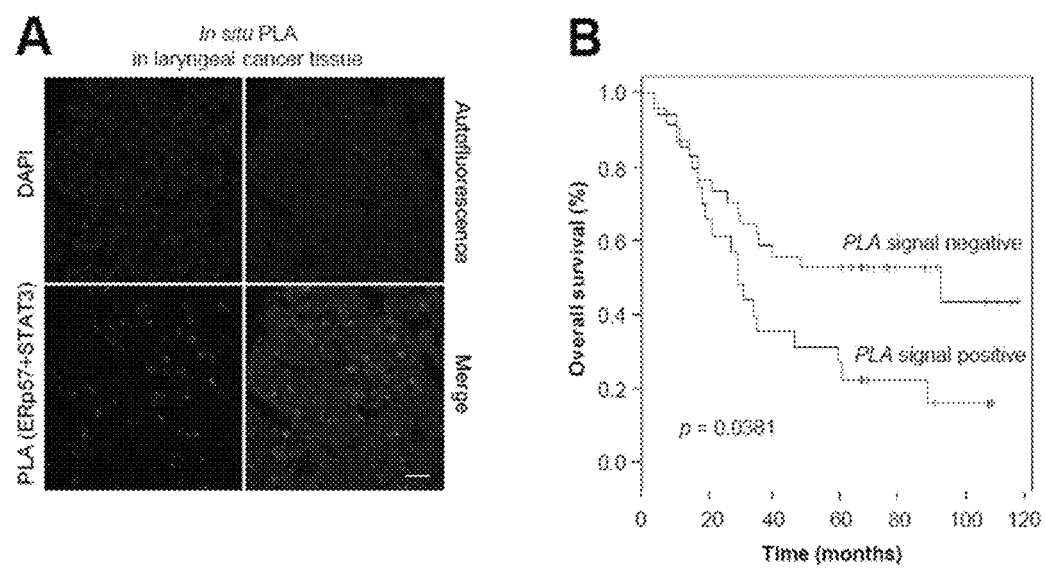
FIG. 6 shows the results of analyzing interactions between ERp57 and STAT3 and relevance regarding prognosis in laryngeal cancer. A of FIG. 6 shows confocal images detecting ERp57, STAT3, and Mcl-1 in laryngeal cancer cells by using anti-ERp57 antibodies (rabbit), anti-STAT3 antibodies (mouse), and Hoechst 33342 (blue signal) according to the PLA analysis; and B of FIG. 6 shows Kaplan-Meier survival curves representing a positive sample and a negative sample in terms of overall survival of ERp57-STAT3 protein complex according to the PLA analysis.

As shown in A of FIG. 6, positive signals were detected in laryngeal cancer tissues, indicating in vivo relevance of ERp57-mediated STAT3 regulation.

As shown in B of FIG. 6, it was also confirmed that high ERp57-STAT3 interactions correlated with reduced overall survival (P=0.0381). Thus, it was confirmed that increased ERp57-mediated STAT3 regulation confers poor prognosis in laryngeal cancer.

As described above, according to the one or more of the above exemplary embodiments, the present inventive concept verifies increased expression of ERp57, ERp57-STAT3 complex, and ERp57-STAT3-Mcl-1 in laryngeal cancer, especially in radioresistant laryngeal cancer and regulation of radioresistance of laryngeal cancer, to diagnose prognosis in laryngeal cancer and radioresistance of laryngeal cancer, thererby further improving the efficacy of radiotherapy.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of in vitro inhibiting the growth of radioresistant laryngeal cancer cells, comprising:
    obtaining a first sample containing human epithelial type 2 (HEp-2) cells;
    obtaining a second sample containing radioresistant human epithelial type 2 (RR-HEp-2) cells;
    irradiating the obtained first and second samples with a Cesium-137 source;
    measuring the protein expression level of ERp57 in the first and second samples;
    comparing measured expression level of ERp57 in the first sample to the second sample;
    determining one having higher expression level of Erp57 among the first and the second samples, wherein the protein expression level of ERp57 is upregulated in the RR-Hep-2 cells compared to the Hep-2 cells; and
    providing a effective amount of an ERp57 inhibitor to the second sample, wherein the growth of radioresistant laryngeal cancer cells is inhibited.

2. The method of claim 1, wherein the ERp57 inhibitor comprises:
    any one of siRNA, shRNA, and antisense oligonucleotide, each of which inhibits the expression of ERp57; and
    a neutralizing antibody binding to ERp57 and inhibiting ERp57 activity.

3. The method of claim 2, wherein the siRNA comprises SEQ ID NOs: 1 or 2.

4. A method of in vitro inhibiting the growth of radioresistant laryngeal cancer cells, comprising:
    obtaining a first sample containing human epithelial type 2 (HEp-2) cells;
    obtaining a second sample containing radioresistant human epithelial type 2 (RR-HEp-2) cells;
    irradiating the obtained first and second samples with a Cesium-137 source;
    measuring the protein expression level of ERp57-STAT3 complex in the first and second samples;
    comparing measured expression level of ERp57-STAT3 complex in the first sample to the second sample;
    determining one having higher expression level of ERp57-STAT3 among the first and the second samples, wherein the protein expression level of ERp57 is upregulated in the RR-Hep-2 cells compared to the Hep-2 cells; and providing a effective amount of an ERp57-STAT3 complex inhibitor which inhibits the STAT3 to the second sample, wherein the growth of radioresistant laryngeal cancer cells is inhibited.

5. The method of claim 4, wherein the ERp57-STAT3 complex inhibitor comprises:

any one of siRNA, shRNA, and antisense oligonucleotide, each of which inhibits the expression of STAT3; and a neutralizing antibody binding to STAT3 and inhibiting STAT3 activity.

6. The method of claim 5, wherein the siRNA comprises SEQ ID NO: 3.

* * * * *

SEQUENCE LISTING

```
<160> NUMBER OF SEQ ID NOS: 14

<210> SEQ ID NO 1
<211> LENGTH: 19
<212> TYPE: RNA
<213> ORGANISM: Artificial Sequence
<220> FEATURE:
<223> OTHER INFORMATION: ERp57 siRNA-1

<400> SEQUENCE: 1
ggacaagacu guggcauau                                                  19

<210> SEQ ID NO 2
<211> LENGTH: 19
<212> TYPE: RNA
<213> ORGANISM: Artificial Sequence
<220> FEATURE:
<223> OTHER INFORMATION: ERp57 siRNA-2

<400> SEQUENCE: 2
gggcaaggac uuacuuauu                                                  19

<210> SEQ ID NO 3
<211> LENGTH: 19
<212> TYPE: RNA
<213> ORGANISM: Artificial Sequence
<220> FEATURE:
<223> OTHER INFORMATION: STAT3 siRNA

<400> SEQUENCE: 3
ccaacgaccu gcagcaaua                                                  19
```

```
<210> SEQ ID NO 4
<211> LENGTH: 21
<212> TYPE: RNA
<213> ORGANISM: Artificial Sequence
<220> FEATURE:
<223> OTHER INFORMATION: Mcl-1 siRNA

<400> SEQUENCE: 4
cccgccgaau ucauuaauuu a                                            21

<210> SEQ ID NO 5
<211> LENGTH: 20
<212> TYPE: DNA
<213> ORGANISM: Artificial Sequence
<220> FEATURE:
<223> OTHER INFORMATION: ERp57 sense primer

<400> SEQUENCE: 5
cctggtgtgg acactgcaag                                              20

<210> SEQ ID NO 6
<211> LENGTH: 20
<212> TYPE: DNA
<213> ORGANISM: Artificial Sequence
<220> FEATURE:
<223> OTHER INFORMATION: ERp57 antisense primer

<400> SEQUENCE: 6
ccctcaagtt gctggctgct                                              20

<210> SEQ ID NO 7
<211> LENGTH: 26
<212> TYPE: DNA
<213> ORGANISM: Artificial Sequence
<220> FEATURE:
<223> OTHER INFORMATION: IL-6 sense primer

<400> SEQUENCE: 7
cctgagaaag gagacatgta acaaga                                       26

<210> SEQ ID NO 8
<211> LENGTH: 26
<212> TYPE: DNA
<213> ORGANISM: Artificial Sequence
<220> FEATURE:
<223> OTHER INFORMATION: IL-6 antisense primer

<400> SEQUENCE: 8
cctgagaaag gagacatgta acaaga                                       26

<210> SEQ ID NO 9
<211> LENGTH: 21
<212> TYPE: DNA
<213> ORGANISM: Artificial Sequence
<220> FEATURE:
<223> OTHER INFORMATION: Mcl-1 sense primer

<400> SEQUENCE: 9
atctctcggt accttcggga g                                            21

<210> SEQ ID NO 10
<211> LENGTH: 21
<212> TYPE: DNA
<213> ORGANISM: Artificial Sequence
<220> FEATURE:
<223> OTHER INFORMATION: Mcl-1 antisense primer
```

```
<400> SEQUENCE: 10
accagctcct actccagcaa c                                             21

<210> SEQ ID NO 11
<211> LENGTH: 23
<212> TYPE: DNA
<213> ORGANISM: Artificial Sequence
<220> FEATURE:
<223> OTHER INFORMATION: VEGF sense primer

<400> SEQUENCE: 11
cgaagtggtg aagttcatgg atg                                           23

<210> SEQ ID NO 12
<211> LENGTH: 25
<212> TYPE: DNA
<213> ORGANISM: Artificial Sequence
<220> FEATURE:
<223> OTHER INFORMATION: VEGF antisense primer

<400> SEQUENCE: 12
ttctgtatca gtctttcctg gtgag                                         25

<210> SEQ ID NO 13
<211> LENGTH: 21
<212> TYPE: DNA
<213> ORGANISM: Artificial Sequence
<220> FEATURE:
<223> OTHER INFORMATION: GAPDH sense primer

<400> SEQUENCE: 13
catctctgcc ccctctgctg a                                             21

<210> SEQ ID NO 14
<211> LENGTH: 21
<212> TYPE: DNA
<213> ORGANISM: Artificial Sequence
<220> FEATURE:
<223> OTHER INFORMATION: GAPDH antisense primer

<400> SEQUENCE: 14
ggatgacctt gcccacagcc t                                             21
```